United States Patent
Soring et al.

(10) Patent No.: US 6,916,296 B2
(45) Date of Patent: Jul. 12, 2005

(54) SYSTEM FOR ANTISEPTIC SURGERY

(75) Inventors: Holger Soring, Quickborn (DE); Jorg Soring, Holm (DE)

(73) Assignee: Soring GmbH Medizintechnik, Quickborn (DE)

( * ) Notice: Subject to any disclaimer, the term of this patent is extended or adjusted under 35 U.S.C. 154(b) by 0 days.

(21) Appl. No.: 10/175,238

(22) Filed: Jun. 18, 2002

(65) Prior Publication Data

US 2003/0023193 A1 Jan. 30, 2003

Related U.S. Application Data

(63) Continuation-in-part of application No. 09/861,765, filed on May 21, 2001.

(51) Int. Cl.$^7$ ................................................. A61H 1/00
(52) U.S. Cl. ................... 601/2; 601/3; 601/4; 600/439; 600/459; 310/311; 310/322; 310/334; 310/340
(58) Field of Search .......................... 601/2–4; 600/439, 600/459; 310/311, 322, 334, 340

(56) References Cited

U.S. PATENT DOCUMENTS

| 3,645,255 | A | | 2/1972 | Robinson |
| 4,331,422 | A | * | 5/1982 | Heyman ..................... 433/125 |
| 4,982,730 | A | * | 1/1991 | Lewis, Jr. .................... 128/24 |
| 5,702,360 | A | * | 12/1997 | Dieras et al. ................. 604/22 |
| 5,735,811 | A | | 4/1998 | Brisken |
| 5,931,805 | A | | 8/1999 | Brisken |

* cited by examiner

Primary Examiner—Shawntina Fuqua
(74) Attorney, Agent, or Firm—Horst M. Kasper

(57) ABSTRACT

A method is furnished for a treatment of septic wounds. A hand piece of a sonotrode is connected to a liquid storage. Access to a wound is furnished to the sonotrode. A liquid atomized by ultrasound is delivered to the wound through a sonotrode channel disposed in the sonotrode. Bacteria in the area of the wound are destroyed by the ultrasound emitted by the sonotrode. The method allows to remove a prosthesis not longer desired from a patient. The area left open by the removed prosthesis and/or a bone is filled with a liquid. The sonotrode is then entered into the liquid for propagating ultrasound through the liquid and thereby destroying bacteria present in the liquid.

27 Claims, 8 Drawing Sheets

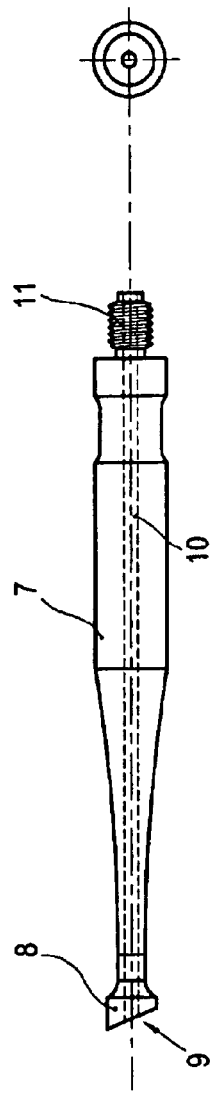
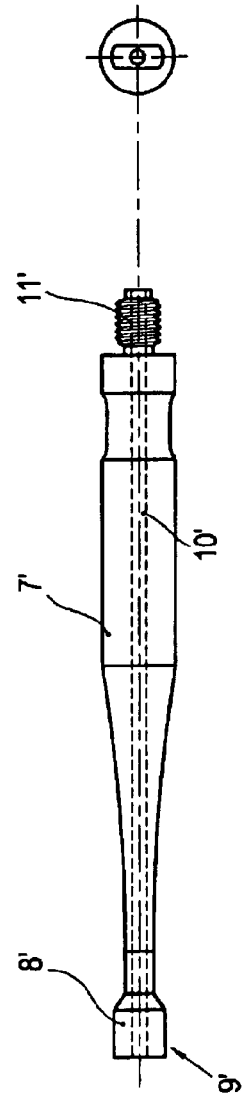
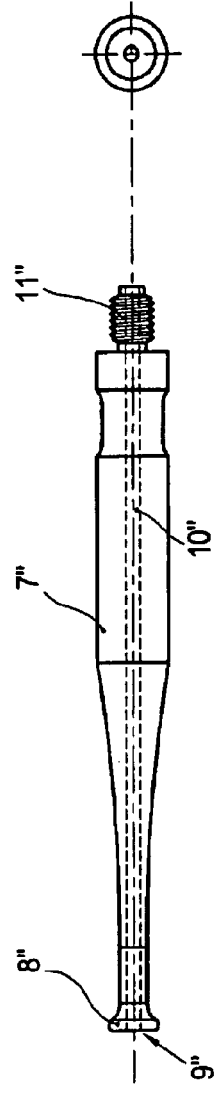
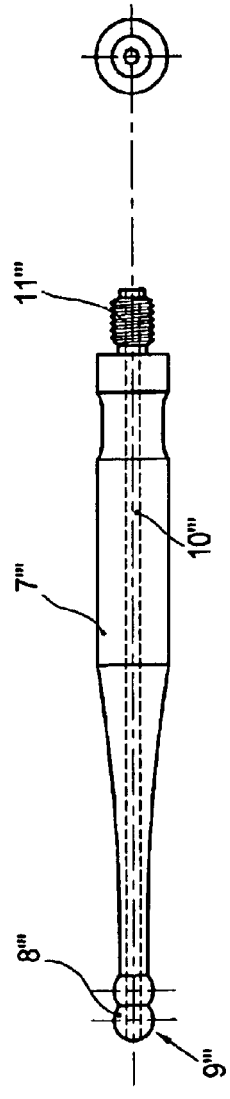

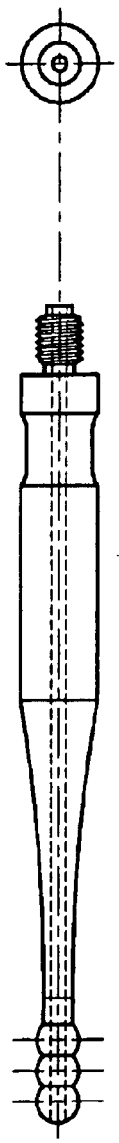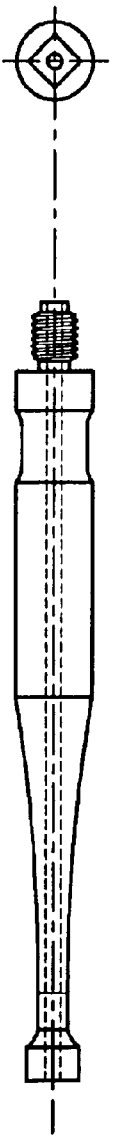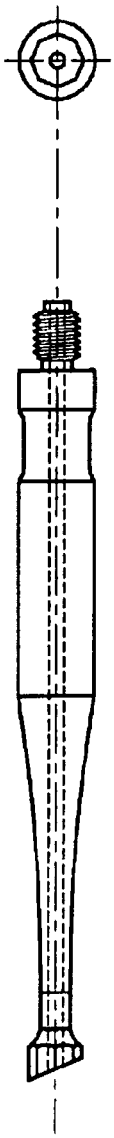
Fig.6a Fig.6b Fig.7a Fig.7b Fig.8a Fig.8b Fig.9a Fig.9b Fig.10a Fig.10b Fig.11a Fig.11b

SYSTEM FOR ANTISEPTIC SURGERY

CROSS-REFERENCE TO THE RELATED APPLICATIONS

This application is a continuation-in-part application of another U.S. patent application filed on May 21, 2001 and bearing Ser. No. 09/861,765. The entire disclosure of this later application, including the drawings thereof, is hereby incorporated in the present application as if fully set forth herein.

BACKGROUND OF THE INVENTION

1. Field of the Invention

The present invention concerns an ultrasonic system for the treatment of septic wounds and for surgical applications, for example of bacterially infected wounds and internal body parts, which comprises a hand piece connected to an ultrasonic generator and a sonotrode attached to the hand piece.

2. Brief Description of the Background of the Invention Including Prior Art

Methods are known for a treatment of septic wounds. However, these methods are not only very painful for the patient, but in addition, very time-consuming and therefore cost intensive. A healing success is not guaranteed in connection with these conventional methods of treatment. Also a transplantation of skin parts from other locations of the body is further required in particular serious cases.

It occurs again and again that artificial limbs and joints such as hip prosthesis, knee prosthesis, or shoulder prosthesis have to be exchanged since a loosening of the prosthesis has occurred based on inflammation.

The surgeon can only mechanically clean the inflamed section after the removal of the old prosthesis according to the presently used methods of operation that is by scraping, by scratching, and by abrading followed with flushing with liquid having antibacterial effects. A treatment with antibiotics after the insertion of the new prosthesis remains without effect, since the antibiotics cannot pass to the boundary layer between prosthesis and bone as well as into the bone and into the bone channels. The path to the boundary layer between prosthesis and bone, in the bone and in the bone channels is blocked still by the cement. Since the bone is not furnished with a sufficient connection to the blood circulation of the patient, and intravenous dispensation has to be excluded.

SUMMARY OF THE INVENTION

1. Purposes of the Invention

It is an object of the present invention to furnish a method for disinfection and destruction of bacteria and germs in surgical operations.

It is another object of the present invention to furnish an ultrasonic apparatus for the treatment of septic wounds, wherein the ultrasonic apparatus provides for a cost favorable method of treatment and where this method of treatment is less painful for the patient.

These and other objects and advantages of the present invention will become evident from the description, which follows.

2. Brief Description of the Invention

The present invention provides a structure of a sonotrode of an ultrasonic apparatus suitable for surgical operations. A surgeon fills a bone with a sterile liquid after removal of an old prosthesis from the bone and the surgeon then enters a sonotrode into the liquid extending into the bone. The sonotrode can by all means have a length from about 25 to 40 cm. The head of the sonotrode preferably is comprised of several balls sequentially following each other. This shape has proven to be particular advantageous, because the ball shaped structure induces an optimum energy flow. The cavitation generated in the liquid by the ultrasonic vibrations leads to a destruction of the bacteria.

This ultrasonic treatment head or sonotrode resolves the recited problem existing and now a channel is furnished for a feeding of rock salt solution and possibly of medical healing agents such as heparin to the surface to be treated, wherein the sonotrode head can form different shapes depending on the method and kind of treatment.

In order to optimize the treatment method, the sonotrode head and the treatment face of the sonotrode have been formed in very different forms adapted to the different body forms and wound forms. The bactericidal, cleaning and massaging effect of the ultrasound are employed in the application of this so-called ultrasonic method.

The direct contact of the treatment face of the outer sonic treatment head with the pain sensitive wound regions is avoided by the employment of liquid aerosols. The microcirculation is stimulated by the application of the ultrasound, that is the infected cells are destroyed by the massaging action of the ultrasound and thus the surface of the wound is cleaned and the wound heals in a short time upon the regular application of the treatment with ultrasound.

In addition to the rock salt solution also medical healing agents such as heparin, antibiotics and the like can be applied through the channel furnished within the sonotrode, which is particularly recommended in cases of difficult accessible areas of infection. Such an ultrasonic treatment is in particular helpful in such cases, where no improvement could be achieved by injections into the area of the wound. The employment of liquids is additionally associated with the advantage that thereby the heat generated during the treatment is dissipated from the sonotrode head.

As was mentioned above, the sonotrode heads or ultrasonic treatment heads of the subject of the present invention are formed very differently. The shape of the sonotrode head and of the treatment surface depend strongly on the position and shape of the wound, in order to assure an optimum employment of the ultrasonic energy. The subject of the present invention is to be explained in more detail by way of the drawings of the various embodiments.

The novel features, which are considered as characteristic for the invention are set forth in the appended claims. The invention itself, however, both as to its construction and its method of operation, together with additional objects and advantages thereof, will be best understood from the following description of specific embodiments, when read in connection with the accompanying drawing.

BRIEF DESCRIPTION OF THE DRAWING

In the accompanying drawing, in which are shown several of the various possible embodiments of the present invention:

FIG. 2a is a schematic side elevational view of a sonotrode with a treatment surface formed inclined relative to the longitudinal axis;

FIG. 2b is a schematic front elevational view onto the front face of the sonotrode according to FIG. 2a;

FIG. 3a is a schematic side elevational view of a sonotrode with a treatment face in the shape of a screwdriver blade;

FIG. 3b is a schematic front elevational view onto the front face of the sonotrode according to FIG. 3a;

FIG. 4a is a schematic side elevational view of a sonotrode with a dish shape treatment face;

FIG. 4b is a schematic front elevational view onto the front face of the sonotrode according to FIG. 4a;

FIG. 5a is a schematic side elevational view of a sonotrode with a ball shaped treatment surface;

FIG. 5b is a schematic front elevational view onto the front face of the sonotrode according to FIG. 5a;

FIG. 6a is a schematic side elevational view of a sonotrode with a three-ball shaped treatment surface;

FIG. 6b is a schematic front elevational view onto the front face of the sonotrode according to FIG. 6a;

FIG. 7a is a schematic side elevational view of a sonotrode with a round flat face treatment surface;

FIG. 7b is a schematic front elevational view onto the front face of the sonotrode according to FIG. 7a;

FIG. 8a is a schematic side elevational view of a sonotrode with a treatment surface formed inclined relative to the longitudinal axis and having a rectangular end face;

FIG. 8b is a schematic front elevational view onto the front face of the sonotrode according to FIG. 8a;

FIG. 9a is a schematic side elevational view of a sonotrode with a square flat face treatment surface;

FIG. 9b is a schematic front elevational view onto the front face of the sonotrode according to FIG. 9a;

FIG. 10a is a schematic side elevational view of a sonotrode with a treatment surface formed inclined relative to the longitudinal axis and having a polygonal face;

FIG. 10b is a schematic front elevational view onto the front face of the sonotrode according to FIG. 10a;

FIG. 11a is a schematic side elevational view of a sonotrode with a polygonal flat face treatment surface;

FIG. 11b is a schematic front elevational view onto the front face of the sonotrode according to FIG. 11a;

DESCRIPTION OF INVENTION AND PREFERRED EMBODIMENT

Figure 1:
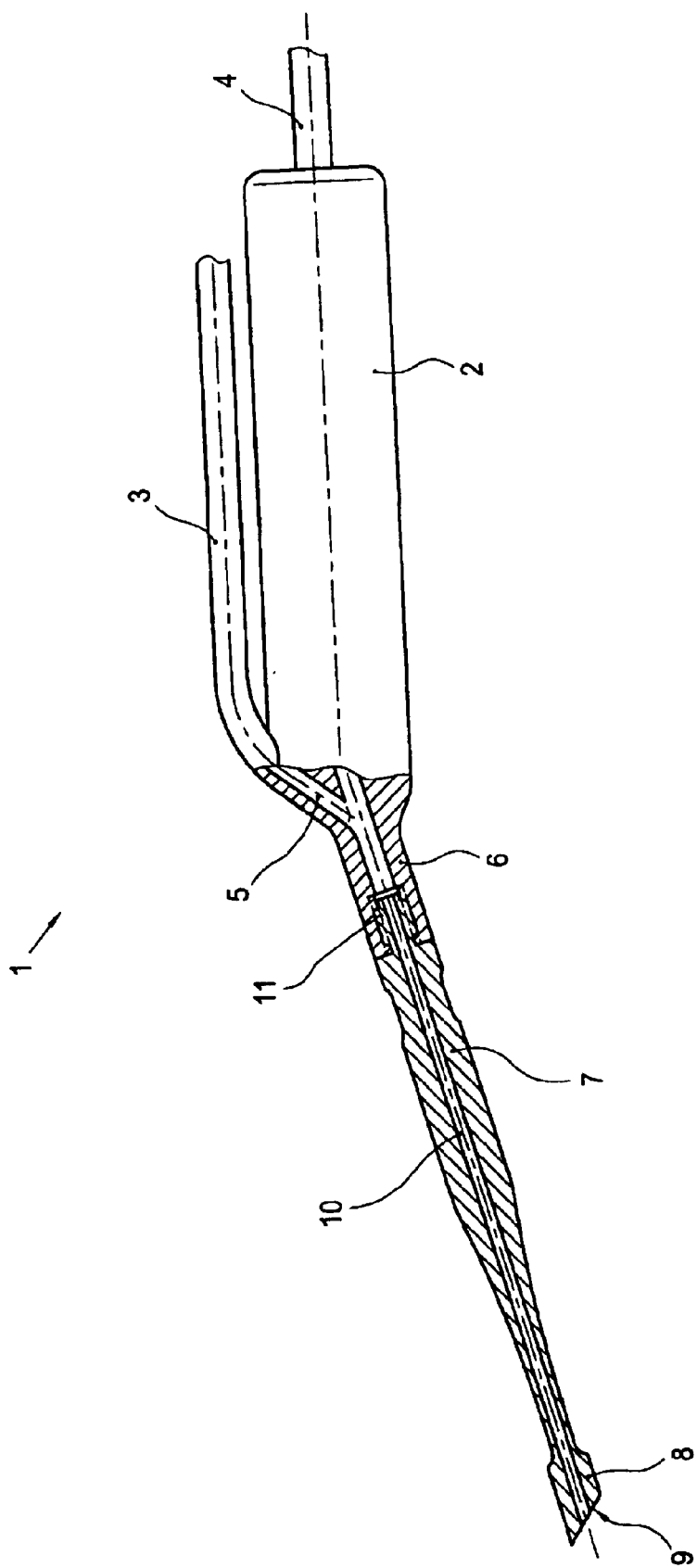
FIG. 1 is a schematic view of a partial longitudinal section through a hand piece with an exchangeable sonotrode head.

In accordance with the present invention there is furnished an ultrasonic apparatus illustrated in FIG. 1 comprising a hand piece (1) within a handle region (2), a connection tube (3) for connecting to a supply tube, wherein rock salt solution and medical healing agents such as heparin, antibiotics and the like are fed through the feed channel (5) to the sonotrode (7) or ultrasonic treatment head. The ultrasound energy is fed to the hand piece (1) through the connection line (4) to the ultrasonic generator in a conventional way.

The hand piece (1) is equipped with a sonotrode receptacle (6), wherein the sonotrode receptacle exhibits a thread for screwing in of the sonotrode (7, 7', 7", 7'''). The respective sonotrode (7,7', 7", 7''') is furnished with an attachment thread (11,11', 11", 11''') corresponding to the thread of the hand piece. The liquid to be fed in to the treatment face (9,9', 9", 9''') is led through the channel (10,10', 10", 10''').

The sonotrode receptacle (6) can be disposed such that a sonotrode (7, 7', 7", 7''') attached to the sonotrode receptacle (6) would exhibit an angle between a longitudinal axis of the sonotrode (7, 7', 7", 7''') and an axis of the handle region (2). The angle between a longitudinal axis of the sonotrode (7, 7', 7", 7''') and an axis of the handle region (2) can be from about 5 to 25 degrees and is preferably from about 10 to 15 degrees. The total length of the handle region (2) can be from about one to two times the length of the sonotrode (7, 7', 7", 7''') and is preferably from about 1.1 to 1.4 times the length of the sonotrode (7, 7', 7", 7''').

The handle region (2) can have its axial direction aligned substantially in parallel to the axial direction of the supply tube (3). The diameter of the handle region (2) can be from about 3 to 5 times the outer diameter of the supply tube (3). The supply tube (3) can be disposed on a side opposite to the side of the sonotrode (7, 7', 7", 7''') relative to the axis of the handle region (2). A connection means can be provided at the handle region near the position of the sonotrode receptacle (6) for connecting the supply tube (3) on a side opposite to the side of the sonotrode (7, 7', 7", 7''') relative to the axis of the handle region (2). The connection means can be associated with a bore hole in the handle region (2) connecting the connection means to the feed channel (5) disposed in a middle of the sonotrode receptacle (6). The diameter of the sonotrode receptacle (6) can be from about two to four times the diameter of the channel (5).

The sonotrodes (7,7', 7", 7''') have a sonotrode channel (10) extending in the longitudinal direction of the sonotrodes (7,7', 7", 7'''). The diameter of the channel (5) has a diameter from about 0.5 to 4 times the diameter of the sonotrode channel (10) and are preferably of substantially the same diameter.

The ends of the sonotrodes (7,7', 7", 7''') on the treatment side can be furnished with very different sonotrode heads (8,8', 8",8'''). For example, FIG. 2 shows a sonotrode head (8) with a cylindrical outer shape. The treatment face (9) is preferably milled and polished at an inclined angle relative to the longitudinal axis. The inclination angle relative to the longitudinal axis of the sonotrode can be from about 30 to 70 degrees and is preferably from about 40 to 60 degrees. It is also conceivable to furnish this face in a concave shape, in order to obtain a direct distribution of the liquid.

FIG. 3a shows a longitudinal view of a sonotrode (7') with an attachment thread (11'), a sonotrode channel (10') and a sonotrode head (8'), wherein the sonotrode head (8') exhibits the shape of a screwdriver blade such that the treatment faces (9') are disposed sideways as can be recognized from FIG. 3b. It is also conceivable in connection with this particular construction that the channel (10') is closed on the front side at the sonotrode head and that instead of the channel (10') there is provided a cross bore hole in the middle through the treatment faces (9').

The sonotrode (7") is equipped with a dish shaped sonotrode head (8") as shown in FIG. 4. This sonotrode is also connected to the hand piece (1) by way of the attachment thread (11").

The treatment liquid is fed to the treatment surface through the channel (10"). This treatment face (9") can be formed of a concave shape. The atomization power of the liquids can be further increased by such a shape of a treatment face. A dissipation of the heat generated by the ultrasound is performed simultaneously with the liquid atomization within the applicator and at the radiating border faces.

The sonotrode (7''') illustrated in FIG. 5 includes a ball shaped sonotrode head (8'''). The sonotrode (7''') can be connected to the hand piece (1) with the attachment thread (11'''). The ball shaped treatment face (9''') is supplied with the treatment liquid through the channel (10'''). Such a ball shaped formed treatment face allows a point precise application of the sonotrode (7''') in the wound region. The sonotrode head can, as shown, be comprised of two balls fitted next to each other or also as a single ball or as three or more balls. The number of the next to each other placed balls influences the intensity and the course of the ultrasound vibrations.

In addition, other formed sonotrode head shapes, such as for example spoon shape or hook shape sonotrode heads, are conceivable corresponding to special requirements in addition to the forms of the sonotrode heads illustrated in FIGS. 2 through 5. Some additional forms of sonotrode heads are shown in FIGS. 6 through 11.

For all illustrated and described forms of the sonotrode heads holds that, a dissipation of the heat generated by the ultrasound is performed simultaneously with the liquid atomization within the applicator and at the radiating border faces. Possibly required touch contacts with the wound region can be performed under low-pain based on the liquid fog present and/or based on the liquid film disposed on the surface. The bactericidal effects of the ultrasound operate sterilizing within the zone treated. While the occurrence of a liquid cavitation contributes to the cleaning of tissue zones disposed on the surface, the forced micro-massaging stimulates the microcirculation in the treatment region based on the high alternating sound pressure.

The wound cavitation processes feature a highly efficient, deep penetrating, and bactericidal effect when subjected to ultrasound assisted wound treatment in addition to mechanical rinsing effects. A special wound treatment solution according to Schikorski can be applied for this purpose. This solution is a modified local tumescence anesthetic to which heparin has been added. Cavitations, which are defined as micro gas bubbles imploding cyclically, cause destruction of bacteria, viruses and fungi. The cavitation effects reach deeper into the wound than pure rinsing effects due to ultrasound pressure. Infected chronic wounds are characterized by an acidic wound environment that causes pain. The traits of aseptic wounds change as the bacteria remnants are broken down and the wound environment turns neutral, starting to become permanently free of pain. The neutral wound base tends to heal more quickly.

The method according to the present invention employs the skills involved in using the sonotrode. In accordance with the present invention a surgeon fills the bone with liquid after removal of an old or no longer suitable prosthesis. The surgeon then enters a sonotrode into the liquid. The liquid will be associated with the bone.

The sonotrode can by all means have a length from about 25 to 40 cm. The head of the sonotrode preferably is comprised of several balls sequentially following each other. This shape has proven to be particular advantageous, because the ball shaped structure induces an optimum energy flow. The cavitation generated in the liquid by the ultrasonic vibrations leads to a destruction of the bacteria. The time duration of employment of the ultrasound sonotrode depends on the extent of the inflammation to be treated, the time period duration can by all means amount to several minutes. Under certain circumstances the step of employing the ultrasound sonotrode is to be repeated prior to the implantation of the new prosthesis.

Then the new prosthesis can be inserted after termination of the ultrasound treatment without that an inflammation has to be feared, in contrast to the conventional method, where frequently residual centers of inflammation remain, which centers of inflammation can then result at best or at worst in new problems. Now a third path of a physical germ and bacteria destruction is opened up by the present invention.

The knowledge available based on the present invention opens new paths for the surgeon in the treatment of other inflammations occurring in the body of a patient. Thus germs of inflammation can be destroyed with the ultrasound method, which germs of an inflammation have led for example to an inflammation of the gums of the teeth, or to an inflammation of the peritoneum (peritonitis) in the abdominal space after an intestinal hernia or gastrocele. Not only are the germs and bacteria destroyed with the ultrasound method, which germs and bacteria multiply in an absence of oxygen, but also those germs and bacteria, which multiply in the presence of air.

It is necessary to open the abdomen and to flush several times the abdominal cavity. After termination of the surgical operation antibiotics are dispensed with a patient for destruction of the germs and bacteria.

Here again the ultrasonic method according to the present invention can be employed by filling the abdominal cavity initially with liquid and then in the following a sonotrode optimized for this application purpose is inserted into the abdominal cavity.

Since an opening of the abdomen is always associated with problems, the use of a sonotrode is disclosed and indicated in case of endoscopic operations.

The ultrasound treatment pulse causes the wound treatment solution to penetrate deeply into the fissures of the tissue. Fibrin deposits and bacteria growth are flushed out. The central liquid supply through the sonotrode probe tip shaft has been developed for tasks where direct application to a specific area is required. The wound treatment solution also contains local anesthetics to immediately relieve the pain. Thrombosis of the granulation capillaries is suppressed by heparinization. This also enhances the formation of new capillaries and thereby speeds up the wound healing process.

The ultrasound assisted wound treatment is associated with a number of advantages. An anaesthetizing wound treatment solution contains heparin. The ultrasonic wound debridement is non-lesional. Bacteria grown and sealing fibrin layers are flushed out. The bacterial effects are highly efficient. The acidic wound environment is neutralized. An enhanced granulation is created by heparinization of the wound. Acute and long term pain are alleviated.

The frequency range of the ultrasonic sound employed can be from 20 to 80 kilo hertz.

The ultrasound assisted wound treatment provides an active treatment of chronic wounds instead of a passive care. The improvement of the wound and the alleviation of the pain are immediate upon application of the ultrasound assisted wound treatment. The wound conditioning and healing occur within a few weeks. The apparatus comprises a small mobile unit allows outpatient treatment as well as therapy in a hospital. The technology is fault tolerant and can be performed by assisting staff. The daily treatment involves extremely short times of for example from about 2 to 5 minutes depending on the size of the wound. The overall costs are maintained low by providing a single purpose apparatus.

Figure 13:
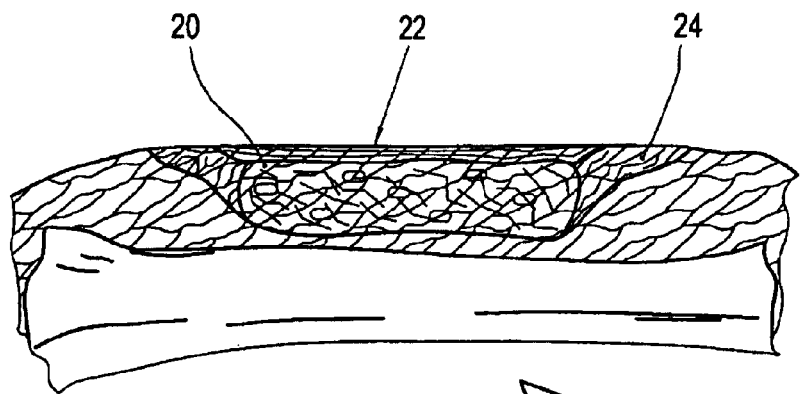
FIG. 13 shows a detail view of the wound of FIG. 12.
Figure 12:
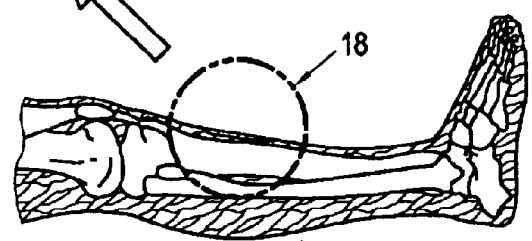
FIG. 12 shows a schematic diagram explaining the location of a wound.

A wound area is presenting the detail 18 of a leg shown in FIG. 12. FIG. 12 in particular shows a schematic diagram explaining the location of a wound in its relation to the detail view of FIG. 13 of the wound. The representation is a chronic wound and its treatment with ultrasound. The wound region 20 is infected by bacteria. The wound is covered by a coating of fibrin 22. The coating of fibrin coloses the area where the bacteria are located and thereby offers the best growth conditions for the bacteria. The surroundings 24 of the wound are also infected.

Figure 15:
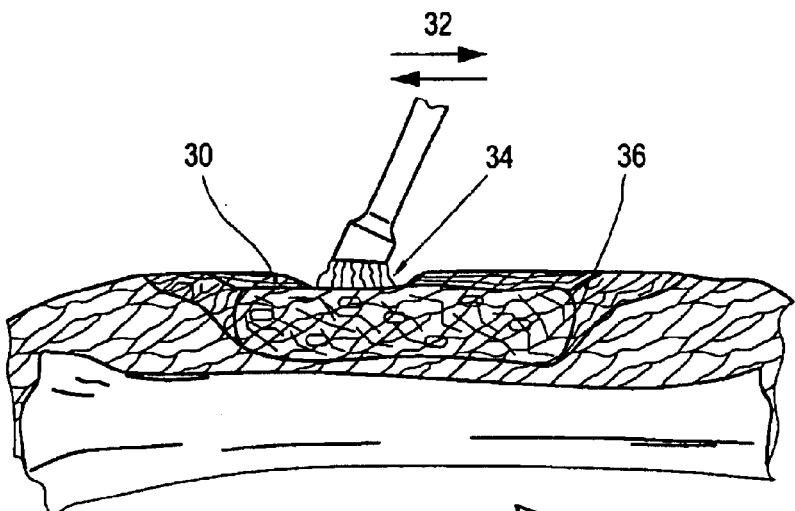
FIG. 15 shows a schematic diagram of an ultrasound therapy of a wound located according to FIG. 14.
Figure 14:
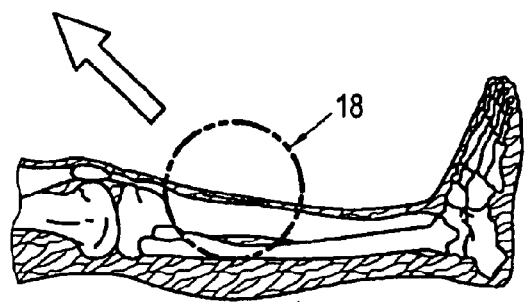
FIG. 14 shows another schematic diagram showing the location of a wound.

FIG. 15 shows a schematic diagram of an ultrasound therapy of a wound located according to FIG. 14. A sonotrode 1 is placed into motion 32 above the area of the wound. The sonotrode provides a spray fog 34 in the area near the head of the sonotrode. The coating of fibrin 30 is removed by the interaction with the ultrasound. The infected wound surrounding 36 is now clean based on the treatement with the sonotrode.

Figure 16:
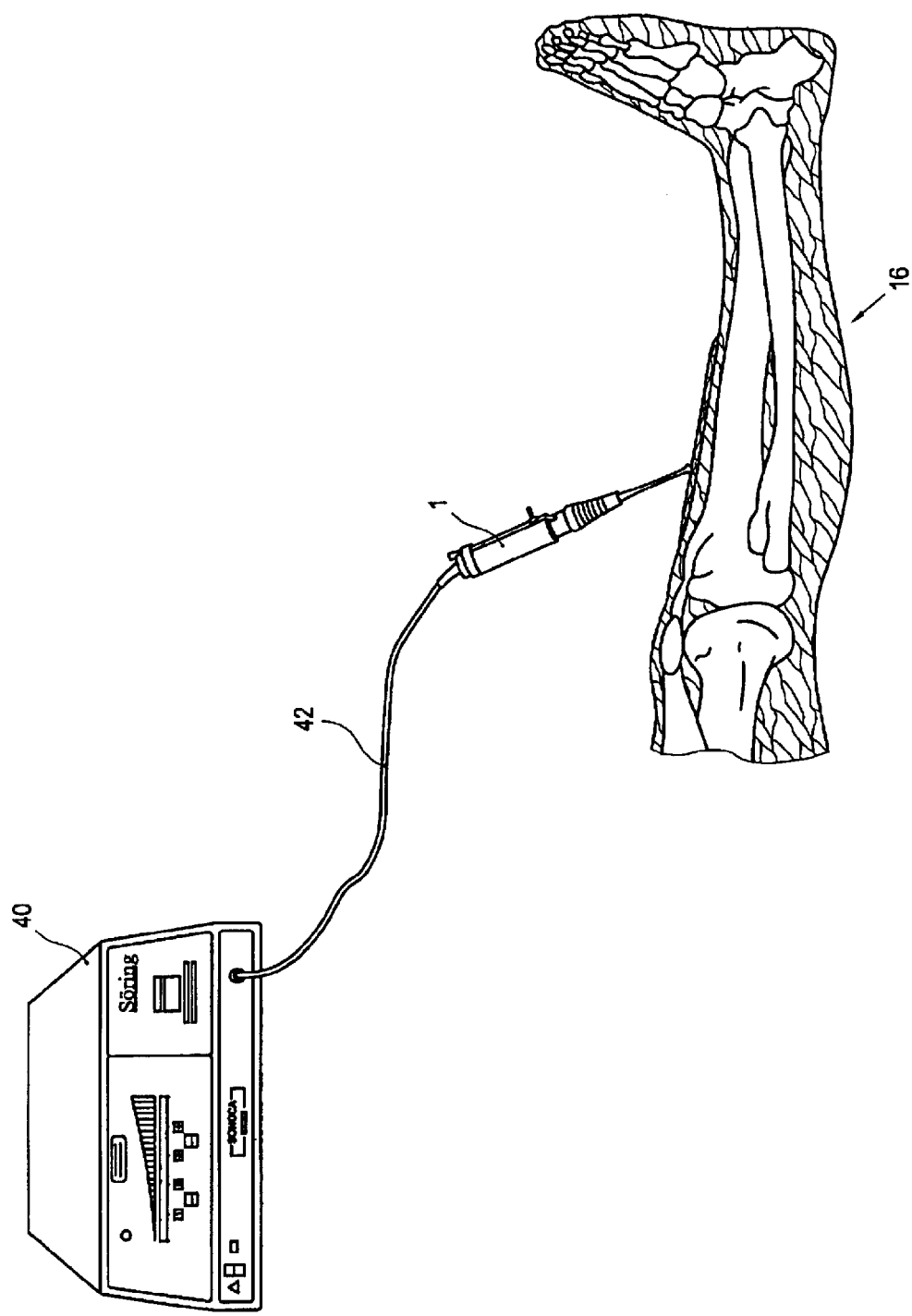
FIG. 16 shows a schematic view of the application of a sonotrode.

The control apparatus 40 of the sonotrode supplies ultrasound power and a spraying agent through a line 42 to the sontrode 1 disposed near a wound on a leg 16. The practical application of a sonotrode is demonstrated in FIG. 16.

In connection with the sonotrode construction, certain tests have been performed relating to the use of the sonotrode. In particular, an investigation into the antibacterial effect of low-frequency ultrasound applied by using a spherical probe-tip (Sonotrode)was performed.

By way of In vitro testing, the time dependence and output dependence of the ultrasound effect as applied to 4 clinically relevant wound germs was determined.

It was a goal of the investigation to determine if the spherical (Sonoca) probe-tip provides a measurable antibacterial effect when immersed for an exposure time applicable for patients in practice. Model: The spherical probe-tip, mounted permanently, is applied to standard germ batches of $5*10^4$ CFU of the respective strain per ml suspended in 15 ml of 0.9% NaCl at 37° C. This occurs in time series and output series. The germs used are *Staphylococcus aureus, Streptococcus pyogenes, Escherichia coli* and *Pseudomonas aeruginosa* that are relevant for wound healing. As test criterion, the number of colony-forming units in a two-dimensional culture (CFU/ml) after the ultrasound impact is used.

Figure 17:
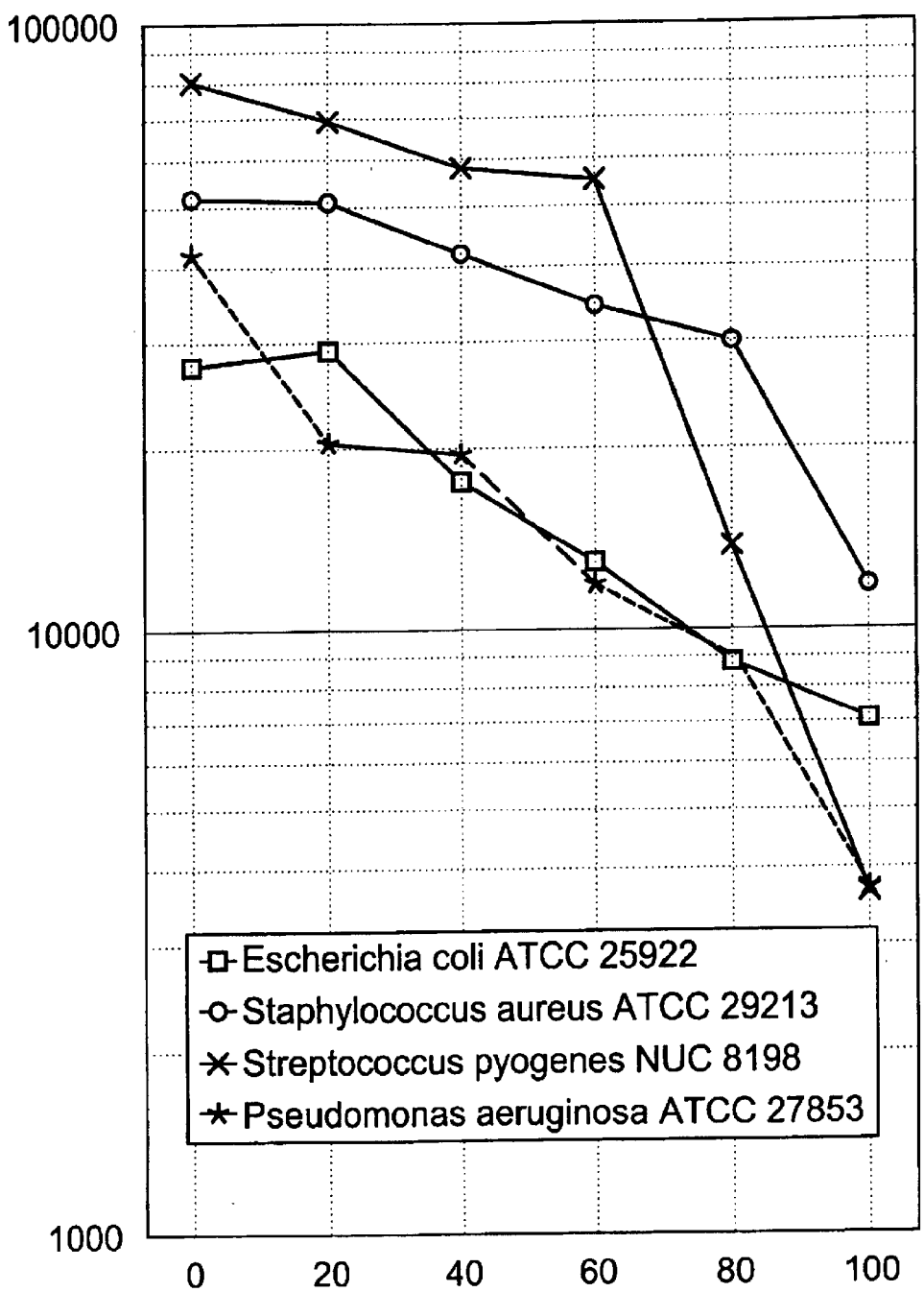
FIG. 17 shows a graphical representation of the germ reduction caused by exposure to low-frequency ultrasound over 60 seconds in relation to the output selected and wherein the individual measuring: points correspond to the median of three individual values.
Figure 18:
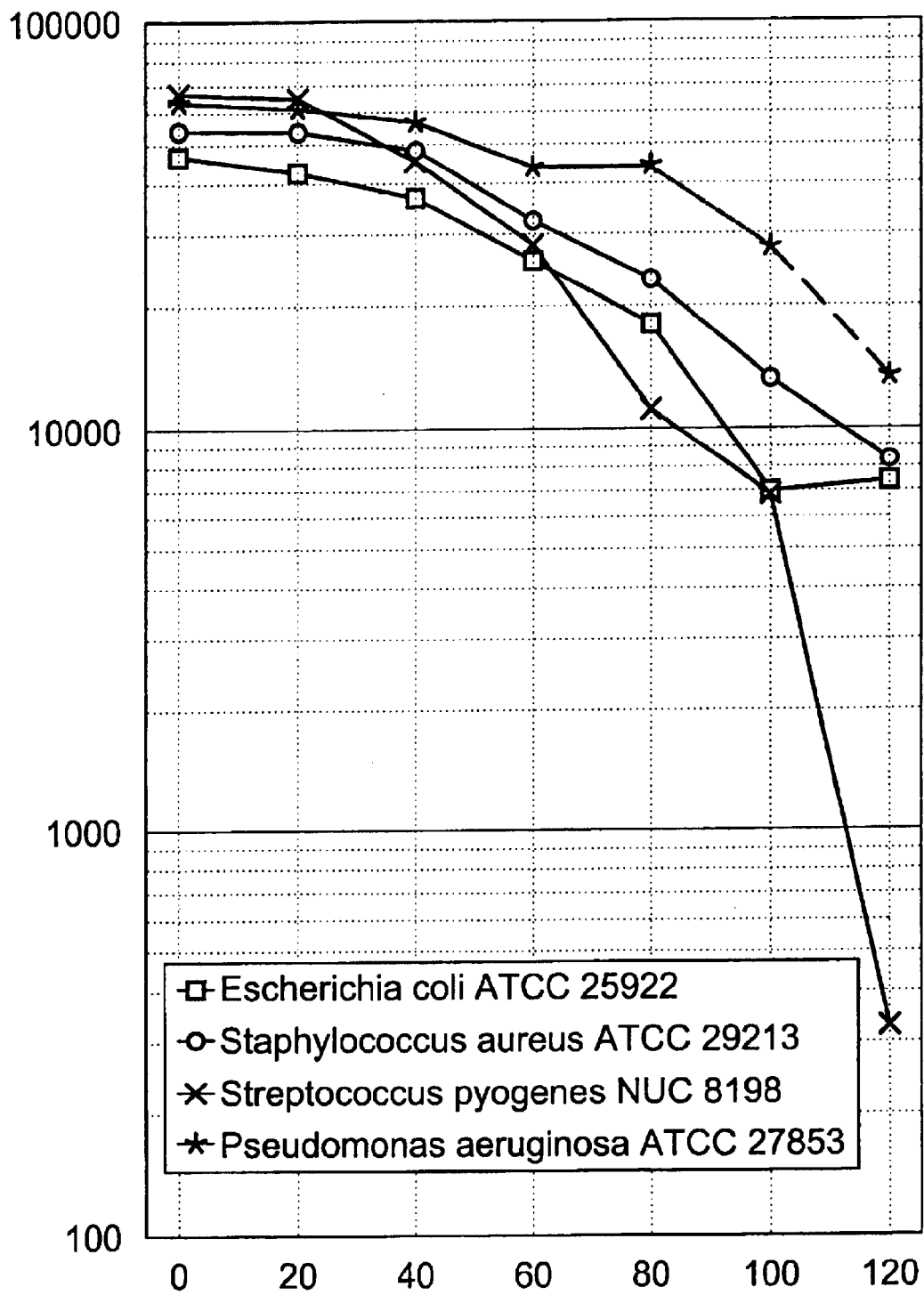
FIG. 18 shows a graphical representation of the germ reduction caused by exposure to low-frequency ultrasound at an output of 60%, in relation to the exposure time (in seconds), wherein the individual measuring points correspond to the median of three individual values.
Figure 19:
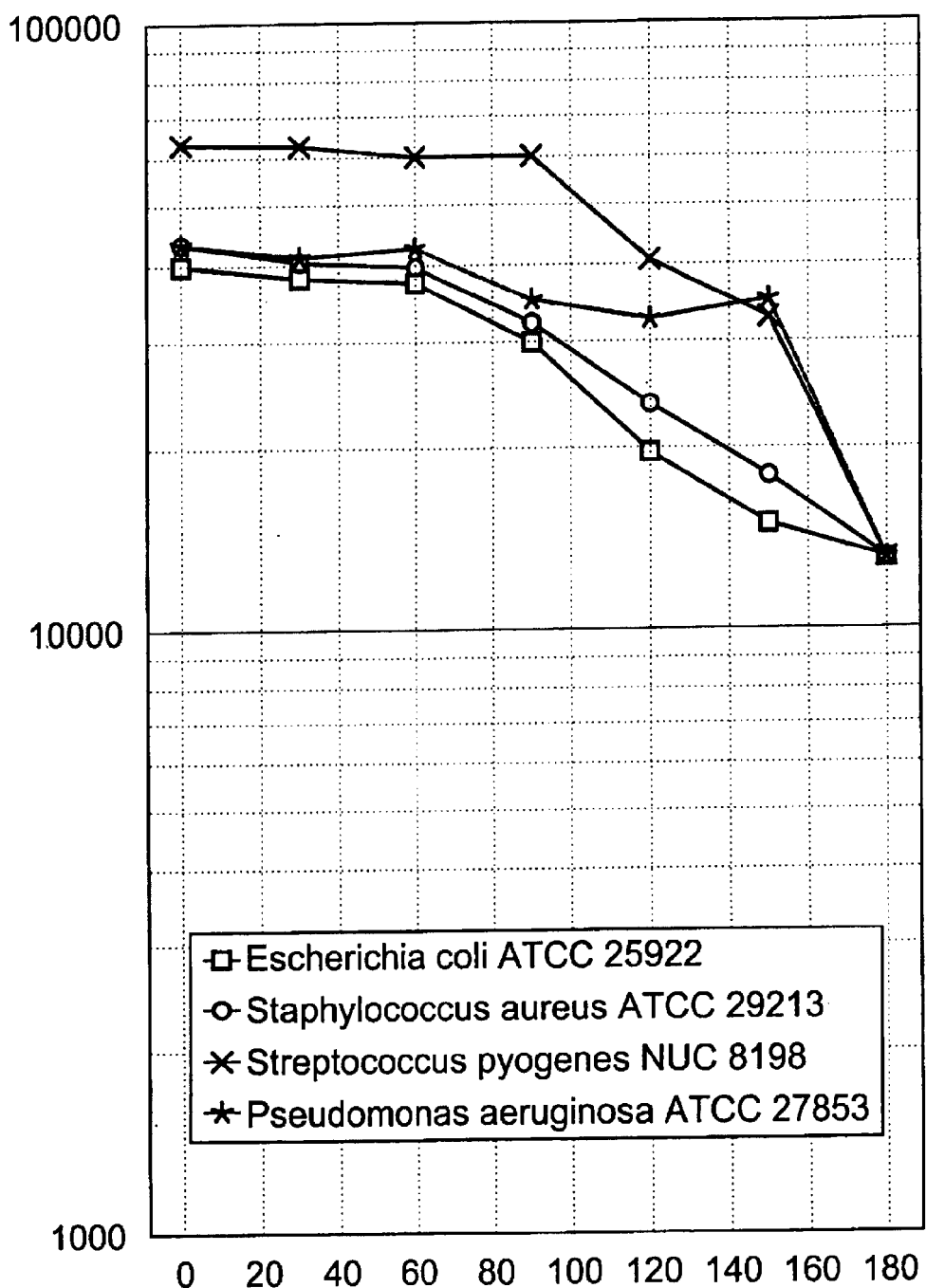
FIG. 19 shows a graphical representation of the germ reduction caused by exposure to low-frequency ultrasound at an output of 20% in relation to the exposure time (in seconds), wherein the individual measuring points correspond to the median of three individual values.

The results are shown in FIGS. 17 through 19.

1. The importance of the output selected at the device was determined and the result is shown in FIG. 17.

A graphical representation of the germ reduction caused by exposure to low-frequency ultrasound over 60 seconds in relation to the output selected is presented in FIG. 17. The individual measuring points of FIG. 17 correspond to the median of three individual values.

A relation can be determined between the output applied and the germ reduction attainable by ultrasound. At an exposure time of 60 seconds, the ultrasound treatment of the standard germ batches of $5*10^4$ CFU/ml resulted in different germ reduction rates for the bacteria species selected. At low outputs of 20 or 40%, a germ reduction of less than 90% (=a power of ten) was attained for all species. In the high output range of 80–100%, however, different results were obtained for the bacteria species selected. Streptococci and pseudomonades proved to be most sensitive, with a germ reduction significantly higher than 90%, whereas the germ reduction by ultrasound did not rise above the power of ten for *Staph. aureus* in this output range either.

2. The ultrasound exposure time at an average output (60%) was tested.

A graphical representation of the germ reduction caused by exposure to low-frequency ultrasound at an output of 60%, in relation to the exposure time (in seconds) is shown in FIG. 18. The individual measuring points correspond to the median of three individual values.

For the exposure time as well, a relation to the attainable germ reduction of the bacteria species used can be determined. First, an average output of 60% was tested. At this output, a maximum kill rate of approx. 90% can be determined after 120 seconds for all bacteria used except for the streptococci which are reduced by more than 99% after this duration. For all germs, short exposure times of less than 60 seconds yield only low kill rates at this output level.

3. The ultrasound exposure time at a low output (20%) was tested.

A graphical representation of the germ reduction caused by exposure to low-frequency ultrasound at an output of 20% in relation to the exposure time (in seconds) is shown in FIG. 19. The individual measuring points correspond to the median of three individual values.

At a low output of 20%, a sufficiently long exposure time obviously yields a moderate germ reduction; however for none of the species tested, a kill rate of 90% was attained after 180 seconds.

The results of these tests lead to the following conclusions. With the spherical probe-tip immersed, a relevant antibacterial effect can be attained in the germ suspension. By using exposure times of 1–3 minutes, a practice-oriented value easily applicable, for example, for a smaller wound was tested. Wound germ indices of $5*10^4$/ml are very common indeed and often are even exceeded in case of very pronounced layers. As the germ colonization plays an important role for wound healing, the germ reduction by application of ultrasound determined may be a reason for improved wound healing by ultrasound-assisted wound treatment. Thus, high output levels clearly are to be preferred. The lower output range on the whole seems to provide an insufficient antibacterial effect. It is uncertain whether a clinically relevant effect can be attained in this range; this deficiency could only be compensated by prolonged exposure times.

It will be understood that each of the elements described above, or two or more together, may also find a useful application in other types of ultrasonic system configurations and wound treatment procedures differing from the types described above.

While the invention has been illustrated and described as embodied in the context of an ultrasonic apparatus for the treatment of septic wounds, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims.

1. A method for the treatment of septic wounds comprising:
   connecting a hand piece of a sonotrode to a liquid storage;
   furnishing access to a wound;
   delivering a liquid atomized by ultrasound to the wound through a sonotrode channel disposed in the sonotrode;
   destructing bacteria in the area of the wound;

destroying bacteria or germs underlying to an inflammation.

2. The method for the treatment of septic wounds according to claim 1 further comprising removing prosthesis not longer desired from a patient;

filling a bone of a patient with a liquid;

entering the sonotrode into the liquid.

3. The method for the treatment of septic wounds according to claim 1 further comprising generating cavitation in the liquid by the ultrasonic vibrations;

destructing of the bacteria by an action of the cavitation on the bacteria.

4. A method for the treatment of septic wounds comprising connecting a hand piece of a sonotrode to a liquid storage;

furnishing access to a wound;

delivering a liquid atomized by ultrasound to the wound through a sonotrode channel disposed in the sonotrode;

destructing bacteria in the area of the wound;

applying ultrasound delivered by the sonotrode for a time period of from about 2 to 10 minutes.

5. The method for the treatment of septic wounds according to claim 1 further comprising repeating a step of employing the ultrasound delivered by the sonotrode prior to an implantation of a new prosthesis.

6. The method for the treatment of septic wounds according to claim 1 further comprising terminating of the delivery of ultrasound for furnishing treatment;

inserting a new prosthesis after terminating of the delivery of ultrasound;

continuing treatment without an inflammation.

7. The method for the treatment of septic wounds according to claim 1 further comprising destroying bacteria or germs underlying to an inflammation selected from the group consisting of an inflammation of the gums of the teeth, an inflammation of the peritoneum in the abdominal space, an inflammation derived from an intestinal hernia, an inflammation derived from a gastrocele, and combinations thereof.

8. A method for the treatment of septic wounds comprising connecting a hand piece of a sonotrode to a liquid storage;

furnishing access to a wound;

delivering a liquid atomized by ultrasound to the wound through a sonotrode channel disposed in the sonotrode;

destructing bacteria in the area of the wound;

destroying bacteria or germs underlying to an inflammation selected from those bacteria or germs multiplying in an absence of air.

9. A method for the treatment of septic wounds comprising connecting a hand piece of a sonotrode to a liquid storage;

furnishing access to a wound;

delivering a liquid atomized by ultrasound to the wound through a sonotrode channel disposed in the sonotrode;

destructing bacteria in the area of the wound;

destroying bacteria or germs underlying to an inflammation selected from those bacteria or germs multiplying in a presence of air.

10. A method for the treatment of septic wounds comprising connecting a hand piece of a sonotrode to a liquid storage;

furnishing access to a wound;

delivering a liquid atomized by ultrasound to the wound through a sonotrode channel disposed in the sonotrode;

destructing bacteria in the area of the wound;

opening an abdominal cavity of a patient;

flushing the opened abdominal cavity several times.

11. The method for the treatment of septic wounds according to claim 1 further comprising terminating a surgical operation of a patient;

dispensing antibiotics to the patient for destroying germs and bacteria.

12. A method for the treatment of septic wounds comprising connecting a hand piece of a sonotrode to a liquid storage;

furnishing access to a wound;

delivering a liquid atomized by ultrasound to the wound through a sonotrode channel disposed in the sonotrode;

destructing bacteria in the area of the wound;

filling an abdominal cavity initially with liquid;

thereafter inserting a sonotrode into the abdominal cavity.

13. A method for the treatment of septic wounds comprising connecting a hand piece of a sonotrode to a liquid storage;

furnishing access to a wound;

delivering a liquid atomized by ultrasound to the wound through a sonotrode channel disposed in the sonotrode;

destructing bacteria in the area of the wound;

performing an endoscopic operation;

employing the sonotrode for destroying bacteria during the endoscopic operation.

14. A method for the treatment of septic wounds comprising contacting a pain sensitive wound region with a treatment face of an outer sonic treatment head while avoiding a direct contact by employing a liquid aerosol; performing a massaging action with ultrasound and thereby cleaning a surface of the pain sensitive wound and thereby healing the pain sensitive wound;

stimulating a microcirculation by applying ultrasound coming from the sonic treatment head; and applying a medical healing agent through a channel furnished within the treatment face.

15. The method for the treatment of septic wounds according to claim 14 wherein the medical healing agent is a member selected from the group consisting of heparin, antibiotics, and mixtures thereof.

16. The method for the treatment of septic wounds according to claim 14 further comprising
　destroying bacteria or germs underlying to an inflammation selected from those bacteria or germs multiplying in an absence of air or in a presence of air.

17. The method for the treatment of septic wounds according to claim 14 further comprising
　opening an abdominal cavity of a patient and flushing the opened abdominal cavity several times;
　filling the abdominal cavity initially with liquid;
　inserting a sonotrode into the abdominal cavity thereafter and performing an endoscopic operation;
　employing the sonotrode for destroying bacteria during the endoscopic operation.

18. The method for the treatment of septic wounds according to claim 14 further comprising
　repeating a step of employing the ultrasound delivered by the sonotrode prior to an implantation of a new prosthesis;
　repeating a step of employing the ultrasound delivered by the sonotrode after to the implantation of the prosthesis, wherein a thrombosis of the granulation capillaries is suppressed by heparinization, and wherein a formation of a new capillaries is enhanced and wherein the formation of new capillaries speeds up a wound healing process.

19. The method for the treatment of septic wounds according to claim 14 further comprising
　performing an active treatment of chronic wounds instead of a passive care, wherein an alleviation of the pain is immediate upon application of ultrasound to the wound;
　performing a daily treatment involving extremely short times of from about 2 to 5 minutes depending on the size of the wound, wherein the wound conditioning and healing occur within a few weeks, and wherein the overall costs are maintained low.

20. The method for the treatment of septic wounds according to claim 14 further comprising removing a coating of fibrin (30) by interaction with ultrasound and a surrounding (36) of an infected wound is left clean based on a treatment with a sonotrode.

21. The method for the treatment of septic wounds according to claim 14 further comprising employing a high output level of the ultrasound.

22. The method for the treatment of septic wounds according to claim 14 further comprising
　employing a lower output level of the ultrasound even though on the whole an insufficient antibacterial effect is provided;
　attaining a clinically relevant effect the lower output level by compensating with a prolonged exposure time.

23. A system for the treatment of septic wounds comprising
　a control apparatus (40), wherein the control apparatus supplies ultrasound power and a spraying agent;
　a sonotrode (1) disposed near an area of a wound on a human body (16), wherein the sonotrode is placed into motion (32) above the area of the wound (18);
　a line (42) connected to the control apparatus (40) and to the sonotrode (1) for delivering ultrasound power and the spraying agent to the sonotrode (1).

24. The system for the treatment of septic wounds according to claim 23, wherein the sonotrode (1) has a length from about 25 to 40 cm, and wherein a head of the sonotrode is comprised of several balls sequentially following each other.

25. The system for the treatment of septic wounds according to claim 23, wherein the control apparatus (40) supplies a frequency range of the ultrasonic sound employed in a range from about 20 to 80 kilo hertz.

26. The system for the treatment of septic wounds according to claim 23, wherein the system for the treatment of septic wounds is formed as a small mobile unit allowing outpatient treatment as well as therapy in a hospital.

27. The system for the treatment of septic wounds according to claim 23 wherein the sonotrode receptacle (6) is disposed such that a sonotrode (7, 7', 7", 7''') attached to the sonotrode receptacle (6) exhibits an angle between a longitudinal axis of the sonotrode (7, 7', 7", 7''') and an axis of the handle region (2), wherein the angle between the longitudinal axis of the sonotrode (7, 7', 7", 7''') and the axis of the handle region (2) is from about 5 to 25 degrees, and wherein the total length of the handle region (2) is from about one to two times the length of the sonotrode (7, 7', 7", 7''').

* * * * *